(12) United States Patent
Palti et al.

(10) Patent No.: US 10,897,713 B2
(45) Date of Patent: Jan. 19, 2021

(54) SAFE CONTROL OF IMPLANTS AND OTHER DEVICES USING ULTRASOUND COMMUNICATION

(71) Applicant: Yoram Palti, Haifa (IL)

(72) Inventors: Yoram Palti, Haifa (IL); Naftaly Sharir, Zicron Yaacov (IL)

(73) Assignee: Terafence Ltd., Haifa (IL)

( * ) Notice: Subject to any disclaimer, the term of this patent is extended or adjusted under 35 U.S.C. 154(b) by 0 days.

(21) Appl. No.: 16/343,222

(22) PCT Filed: Oct. 22, 2017

(86) PCT No.: PCT/IB2017/056557
§ 371 (c)(1),
(2) Date: Apr. 18, 2019

(87) PCT Pub. No.: WO2018/073814
PCT Pub. Date: Apr. 26, 2018

(65) Prior Publication Data
US 2019/0240495 A1 Aug. 8, 2019

Related U.S. Application Data

(60) Provisional application No. 62/411,644, filed on Oct. 23, 2016.

(51) Int. Cl.
*A61N 1/372* (2006.01)
*A61N 1/37* (2006.01)
(Continued)

(52) U.S. Cl.
CPC .............. *H04W 12/08* (2013.01); *A61N 1/37* (2013.01); *A61N 1/37211* (2013.01); *A61N 1/37217* (2013.01); *A61B 5/0015* (2013.01)

(58) Field of Classification Search
CPC ................ A61N 1/37254; A61N 1/362; A61N 1/37217; A61N 1/3956; A61N 1/40
See application file for complete search history.

(56) References Cited

U.S. PATENT DOCUMENTS

| 2004/0202339 A1 | 10/2004 | O'Brien et al. |
| 2008/0071328 A1 | 3/2008 | Haubrich et al. |
(Continued)

OTHER PUBLICATIONS

Galluccio et al., "Challenges and Implications of Using Ultrasonic Communications in Intra-body Area Networks," 2012 9th Annual Conference on Wireless On-Demand Network Systems and Services (WONS), pp. 182-189.
(Continued)

*Primary Examiner* — Paula J Stice
(74) *Attorney, Agent, or Firm* — Potomac Law Group, PLLC

(57) ABSTRACT

Medical devices that have been implanted into human bodies (as well as other devices that have been implanted into other objects) and are controllable via RF commands are subject to intentional tampering and unintentional interference. This drawback can be avoided by designing the implanted system so that either (a) the implanted system can only be controlled via ultrasound signals, or (b) the implanted system can only be controlled via non-ultrasound signals (e.g., RF signals) after the system has been unlocked in response to receipt of a particular ultrasound signal. Because ultrasound waves at the relevant frequencies (e.g., 1-5 MHz) can only enter a body when an ultrasound transmitter is positioned in direct contact with the body, these configurations provide a significant amount of additional security.

23 Claims, 6 Drawing Sheets

(51) Int. Cl.
*A61B 5/00* (2006.01)
*H04W 12/08* (2009.01)

(56) References Cited

U.S. PATENT DOCUMENTS

| | | |
|---|---|---|
| 2009/0270949 A1 | 10/2009 | Kalpin et al. |
| 2012/0215285 A1* | 8/2012 | Tahmasian ........... H04B 5/0037 |
| | | 607/59 |
| 2016/0250486 A1* | 9/2016 | Yoder .................... G16H 40/63 |
| | | 340/870.07 |

OTHER PUBLICATIONS

International Search Report and Written Opinion issued for application No. PCT/IB2017/056557, dated Oct. 15, 2018.
Partial International Search Report issued in application No. PCT/IB2017/056557 dated Aug. 8, 2018.

* cited by examiner

SAFE CONTROL OF IMPLANTS AND OTHER DEVICES USING ULTRASOUND COMMUNICATION

CROSS REFERENCE TO RELATED APPLICATIONS

This application is a US national stage filing under 35 U.S.C. § 371 of International Application No. PCT/IB2017/056557, filed Oct. 22, 2017, which claims the benefit of U.S. Provisional Application 62/411,644 filed Oct. 23, 2016, each of which is incorporated herein by reference in its entirety.

BACKGROUND

The worldwide spread of billions of computers, tablets, smart phones, etc. all connected by the internet is well established. Recently in parallel with the above, the ability to interconnect with environment is rapidly spreading to numerous other types of devices. Thus, there is a growing ability to connect with and control a wide variety of devices, from home appliances, through vehicles to medical diagnostic and treatment devices. The latter may be located in hospitals, clinics, a patients' home, and even wearable and implanted devices. But this interconnectivity has an associated risk. More specifically, a danger exists that an interconnected device may be hijacked by an unauthorized third party (e.g., hackers, terrorists, etc.). This risk can be particularly problematic and/or dangerous in the context of medical implants.

SUMMARY OF THE INVENTION

One aspect of the invention is directed to a first system for implementing secure communication with an implanted device. This first system includes an implantable apparatus and on auxiliary apparatus. The implantable apparatus includes an implantable device configured for implantation into an object, the implantable device having at least one control input. The implantable device is controllable by applying at least one electrical control signal to the at least one control input. The implantable apparatus also includes a first ultrasound transducer that generates a first electrical output signal in response to a first incoming ultrasound signal. The implantable apparatus also includes a first ultrasound frequency receiver that generates, based on the first electrical output signal, first data corresponding to commands that have been encoded onto the first incoming ultrasound signal. The implantable apparatus also includes a first controller configured to (a) generate, based on the first data, the at least one electrical control signal, and (b) to apply the generated at least one electrical control signal to the at least one control input of the implantable device. The implantable apparatus is configured to ignore all attempts to control the implantable device via RF signals. The auxiliary apparatus includes a second controller configured to generate commands for controlling the implantable device, a first ultrasound frequency transmitter that encodes the commands generated by the second controller onto a first driving signal, and a second ultrasound transducer that generates a second ultrasound output signal in response to the first driving signal.

In some embodiments of the first system, the implantable device lacks hardware that is capable of receiving control instructions via RF signals. In some embodiments of the first system, the implantable device includes an RF receiver that has been disabled.

In some embodiments of the first system, the first controller is further configured to generate second data that is indicative of receipt of the first data. In these embodiments, the implantable apparatus further comprises (a) a second ultrasound frequency transmitter that encodes the second data onto a second driving signal, and (b) a third ultrasound transducer that generates a third ultrasound output signal in response to the second driving signal. In these embodiments, the third ultrasound output signal has frequency and amplitude characteristics that permit the third ultrasound output signal to reach an external surface of the object. Optionally, in these embodiments, (i) the auxiliary apparatus may further include a fourth ultrasound transducer arranged to detect the third ultrasound output signal when the fourth ultrasound transducer is placed in acoustic contact with a surface of the object, and to generate a fourth electrical output signal that corresponds to the third ultrasound output signal; and (ii) the auxiliary apparatus further includes a second ultrasound frequency receiver that generates, based on the fourth electrical output signal, fourth data; the fourth data is provided to the second controller, and the fourth data corresponds to the second data.

In some embodiments of the first system, the auxiliary apparatus further includes an RF receiver, and the implantable apparatus further includes an RF transmitter capable of communicating with the RF receiver.

In some embodiments of the first system, the auxiliary apparatus further includes (a) a driver that generates an ultrasound frequency output and (b) a third ultrasound transducer that generates a third ultrasound output signal in response to the ultrasound frequency output generated by the driver, and the second controller is configured to selectively activate the driver. In these embodiments, the implantable apparatus further comprises a fourth ultrasound transducer operatively connected to a wake-up circuit, wherein the wake-up circuit is configured to (i) harvest ultrasound energy arriving at the fourth ultrasound transducer and (ii) generate a wake-up signal for the implanted device from the harvested ultrasound energy.

In some embodiments of the first system, the object is a human body. In some embodiments of the first system, the first ultrasound frequency transmitter has an operating frequency between 1-5 MHz.

Another aspect of the invention is directed to a first implantable apparatus that comprises an implantable device configured for implantation into an object, the implantable device having at least one control input, wherein the implantable device is controllable by applying at least one electrical control signal to the at least one control input. The first implantable apparatus also comprises an ultrasound transducer that generates an electrical output signal in response to an incoming ultrasound signal. The first implantable apparatus also comprises an ultrasound frequency receiver that generates, based on the electrical output signal, first data corresponding to commands that have been encoded onto the incoming ultrasound signal. The first implantable apparatus also comprises a controller configured to (a) generate, based on the first data, the at least one electrical control signal, and (b) to apply the generated at least one electrical control signal to the at least one control input of the implantable device. The first implantable apparatus is configured to ignore all attempts to control the implantable device via RF signals.

In some embodiments of the first implantable apparatus, the implantable device lacks hardware that is capable of receiving control instructions via RF signals.

In some embodiments of the first implantable apparatus, the implantable device includes an RF receiver that has been disabled. In some of these embodiments, the RF receiver is disabled by shielding that prevents RF signals from arriving at the RF receiver.

In some embodiments of the first implantable apparatus, the implantable device comprises a pacemaker. In some embodiments of the first implantable apparatus, at least one of the ultrasound frequency receiver and the controller is configured to implement a secure communication protocol.

In some embodiments of the first implantable apparatus, the controller is further configured to generate second data that is indicative of receipt of the first data. In these embodiments, the implantable apparatus further comprises (a) an ultrasound frequency transmitter that encodes the second data onto a driving signal, and (b) an ultrasound transducer that generates an ultrasound output signal in response to the driving signal. The ultrasound output signal has frequency and amplitude characteristics that permit the ultrasound output signal to reach an external surface of the object.

In some embodiments of the first implantable apparatus, the implantable device includes an RF transmitter capable of communicating with an RF receiver that is positioned outside the object. In some embodiments of the first implantable apparatus, the object is a human body.

Another aspect of the invention is directed to a second system for implementing secure communication with an implanted device. This second system comprises an implantable apparatus and an auxiliary apparatus. The implantable apparatus includes an implantable device configured for implantation into an object, the implantable device having an RF transceiver and at least one control input, wherein the implantable device is controllable by applying at least one electrical control signal to the at least one control input. The implantable apparatus also includes a first ultrasound transducer that generates a first electrical output signal in response to a first incoming ultrasound signal. The implantable apparatus also includes a first ultrasound frequency receiver that generates, based on the first electrical output signal, first data corresponding to commands that have been encoded onto the first incoming ultrasound signal. The implantable apparatus also includes a first controller configured to (a) generate, based on the first data, the at least one electrical control signal, and (b) to apply the generated at least one electrical control signal to the at least one control input of the implantable device. The implantable device is configured to keep the RF transceiver disabled until the at least one electrical control signal generated by the first controller includes an enable command, and to temporarily enable the RF transceiver after the at least one electrical control signal generated by the first controller includes an enable command. The auxiliary apparatus includes a second controller configured to generate commands for controlling the implantable device; a first ultrasound frequency transmitter that encodes the commands generated by the second controller onto a first driving signal; and a second ultrasound transducer that generates a second ultrasound output signal in response to the first driving signal.

In some embodiments of the second system, the auxiliary apparatus further includes an RF transceiver. In some embodiments of the second system, the object is a human body. In some embodiments of the second system, at least one of the first ultrasound frequency receiver and the first controller is configured to implement a secure communication protocol. In some embodiments of the second system, the first ultrasound frequency transmitter has an operating frequency between 1-5 MHz.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
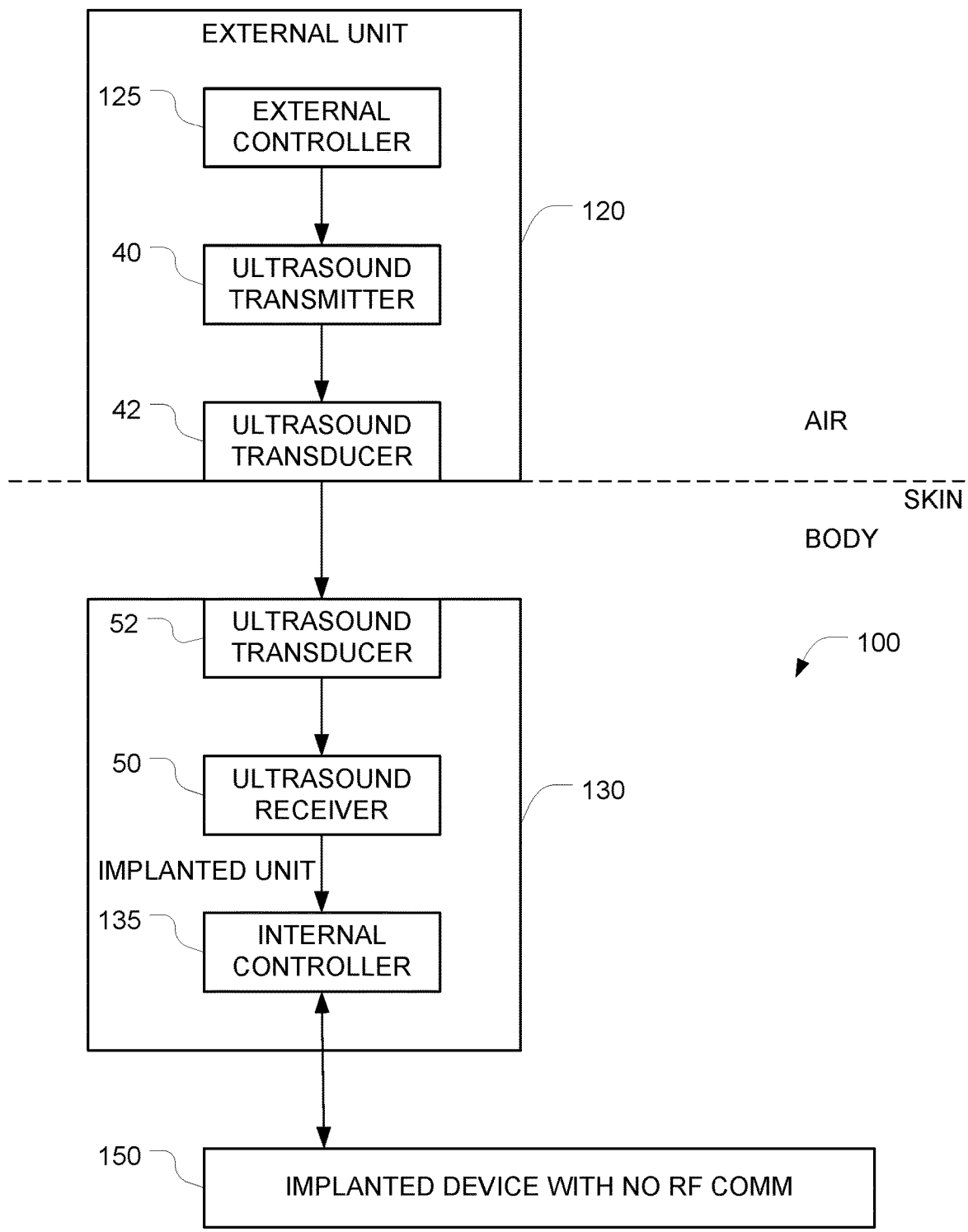
FIG. 1 depicts an example of a system for implementing secure ultrasound communication with an implanted device.

This application relates to the available ability to remotely control medical implants, such as pace-makers, pressure sensors, CNS stimulators, infusion pumps, etc. While implants usually function autonomously, from time to time their function has to be modified from the outside or from another implant. For example, in the case of pace-makers such control can be used to adjust the pacing rate or stimulating pulse characteristics, or in CRT pacers for resynchronization of pacing of the different cardiac chambers, etc. However, a significant downside exists in remotely controllable systems, because the remote control ability opens the possibility to unauthorized manipulation (intentional or accidental) of medical data or treatment, which can pose a very serious threat to the health or life of the users. In addition, electromagnetic detectors such as those used in airports, may also pose a threat. As practically all these devices are controlled by electronic means, hackers and terrorists may gain access to such systems using the net or other RF means and thus pose a significant threat.

The embodiments described herein overcome this danger, by ensuring that the only way to access and control the relevant device, such as an implant, is by mechanical waves such as ultrasound. In the case of medical implants because the mechanical impedance of the human body is very different from that of the ambient air, there is an impedance mismatch that prevents the penetration of the pressure waves from the air into the body, thus protecting it from remote interference with the implant function. Thus, to control an implanted ultrasound activated device, in practice, one has to make contact with the body.

To maximize the power transfer or minimize signal reflection from the load there should be an impedance match. For example, the mechanical impedance of air to MHz range ultrasound waves is $4\times10^2$ (kg/m$^2$-sec) while that of water is $1.5\times10^6$. This fact results in transmission of only 0.1% of the energy across the interface. Similarly, for example, the impedance of muscle and fat are very similar and close to that of water: $1.7\times10^6$ and $1.3\times10^6$ (kg/m$^2$-sec) correspondingly, and therefore the transmission across the soft tissue/water interface is 99.77%. Note that the impedance of metals, aluminum for example is $17\times10^6$ (kg/m$^2$-sec), i.e. fairly close to that of human tissue, and very different from air. Thus, metal enclosed devices with ultrasound sensors are well protected from both air-born ultrasound and RF waves.

In view of the above, the only practical way to control an implant using an ultrasound signal is to position an ultrasound transducer in firm contact (preferably with intervening gel) with the subject's skin. The embodiments described below take advantage of this situation by designing the system so that either (a) the system can only be controlled via ultrasound signals, or (b) the system can only be controlled via non-ultrasound signals (e.g., RF) after the system has been unlocked in response to receipt of a particular ultrasound signal.

In the case of other devices such as home appliances, vehicles, industrial machines, etc. ultrasound waves travelling in the ambient air may reach the device, be picked up and affect any sensor or other element positioned at its surface. To minimize this possibility, the ultrasound sensors, or inputs by means of which the device can be controlled should be protected. Such protection should mimic the human implant situation: all contacts with the device, its inputs and sensors should be encapsulated within a medium which poses a mechanical impedance mismatch with the surroundings, for example: water, gels or the like for air-born ultrasound, or air screen protection for water immersed systems. In such systems the ultrasound energy will be mostly reflected at the surface.

In a first example of a secure communication system using ultrasound, a device is implanted in a living body (which is similar in its mechanical wave conduction and impedance properties to water) where communication can be achieved only by direct contact.

Note that the impedance matching level of protection described herein may be used as the only security mechanism, or in alternative embodiments it may be used in addition to additional security measures (e.g., encryption, etc.).

FIG. 1 depicts an example of a system for implementing secure communication with an implanted device 150 that have been implanted into an object (e.g., a human body). In this example, the implanted device 150 can only be controlled via ultrasound signals, and it is impossible to control the implanted device 150 using RF signals.

The system includes an implantable apparatus 100 and an external unit 120 (also referred to herein as an auxiliary apparatus). The implantable apparatus 100 includes the implantable device 150 and additional implanted components 130, both of which are configured for implantation into an object (e.g., a human body). Examples of devices that can be implanted include, but are not limited to, pacemakers, infusion pumps, pressure sensors, etc. The implantable device 150 has at least one control input, and the implantable device 150 is controlled by the additional implanted components 130 via at least one electrical control signal that is applied to the at least one control input. The implantable apparatus 100 is configured to ignore all attempts to control the implanted device 150 via RF signals. This may be accomplished, for example, by starting with a conventional implanted device (e.g., a pacemaker) that is controllable via RF signals, and disabling the RF section of the device either in software (e.g. firmware), in hardware (e.g. by grounding a control line), or by surrounding the implanted device by suitable shielding that prevents RF energy from reaching the implanted device. Alternatively, this may be accomplished by omitting the RF circuitry entirely from the implanted device.

Because it is impossible to control the implanted device 150 via RF, an alternative signal path must be provided in order to obtain control of the implanted device 150. As noted above, the implantable device 150 has at least one hardwired control input, and the implantable device is controllable by applying at least one electrical control signal to the at least one hardwired control input. And it is this at least one hardwired control input that is used to control the implantable device 150. Note that the software and or hardware of the implantable device 150 must be configured to respond to commands that are received via this at least one hardwired control input.

In the FIG. 1 embodiment, the alternative signal path that is used to control the implanted device 150 comprises the additional implanted components 130. In the illustrated example, these additional implanted components 130 comprise a first ultrasound transducer 52, a first ultrasound frequency receiver 50, and a first controller 135 (also referred to herein as an internal controller). These additional implanted components 130 may be housed in a housing that is separate from the housing of the implanted device 150. In alternative embodiments, the implanted device 150 and the additional implanted components 130 may be housed together in a single housing.

The external unit 120, which is positioned outside the object (e.g. a human body) controls the implanted device 150 by coupling ultrasound waves into the object so that those ultrasound waves can travel through the object and arrive at the implanted apparatus 100. After they reach the implanted apparatus 100, the ultrasound waves are converted to an electrical signal by the ultrasound transducer 52, and that electrical signal is received by the ultrasound receiver 50. The output of the ultrasound receiver 50 is provided to an internal controller 135 which, in turn, generates hardwired control signals that are provided to the implanted device 150. The external unit 120 is preferably housed in an appropriate housing that makes it possible to bring the ultrasound transducer 42 into contact with the surface of the object (e.g., the surface of the subject's skin). This ultrasound transducer 42 is driven by an ultrasound transmitter 40 which, in turn, is controlled by the external controller 125 within the external unit 120.

The first ultrasound transducer 52 is positioned with respect to the housing so that incoming ultrasound signals traveling through the object will arrive at the first ultrasound transducer 52. The first ultrasound transducer 52 generates a first electrical output signal in response to these first incoming ultrasound signals. The first ultrasound frequency receiver 50 generates, based on the first electrical output signal, first data corresponding to commands that have been encoded onto the first incoming ultrasound signal. The ultrasound receiver 50 includes whatever components are necessary to extract the first data that is encoded in the first electrical output signal that it receives. Examples include amplification, signal shaping, demodulation, analog to digital conversion, and other functions that will be apparent to persons skilled in the relevant arts.

The ultrasound receiver 50 outputs the first data to the first controller 135. The first controller 135 is configured to (a) generate, based on the first data, the at least one electrical control signal, and (b) to apply the generated at least one electrical control signal to the at least one control input of the implantable device 150. The implantable device 150 will then respond to those commands.

The auxiliary apparatus 120 includes a second controller 125 (also referred to herein as an external controller) configured to generate commands for controlling the implantable device 150. Control of the auxiliary apparatus 120 may be effectuated using any appropriate user interface, the details of which will be apparent to persons skilled in the relevant arts. The auxiliary apparatus 120 also includes a first ultrasound frequency transmitter 40 that encodes the commands generated by the second controller onto a first driving signal, and a second ultrasound transducer that generates a second ultrasound output signal in response to the first driving signal. It is this second ultrasound output signal that is transmitted into the object (e.g. into the subject's body).

When the auxiliary apparatus 120 is placed against the surface of the object (e.g., against a human subject skin) so that the ultrasound transducer 42 is in acoustic contact with the surface of the object, the auxiliary apparatus 120 can transmit commands into the object via ultrasound. Optionally, ultrasound gel (e.g., similar to the gels used for medical sonograms) may be used to enhance the acoustic coupling between the ultrasound transducer 42 and the surface of the object.

The signal path from the external controller 125 to the internal controller 135 includes an ultrasound frequency transmitter 40 and an ultrasound frequency receiver 50. Although the exact nature of the transmitter 40 and the receiver 50 is not critical, the receiver 50 should be designed to be the counterpart of the transmitter 40. For example, if the transmitter 40 uses a particular approach to encode the commands that it receives from the second controller 125, the receiver 50 should use the counterpart of that approach to decode the electrical signals that it receives. Examples of suitable approaches for encoding and decoding include digital modulation/demodulation techniques (including but not limited to amplitude-shift keying, phase-shift keying, pulse-position modulation, etc.) and analog modulation/demodulation techniques (including but not limited to amplitude modulation, frequency modulation, phase modulation, etc.). Optionally, differential pulse position modulation may be used for implementing synchronization. In some embodiments, the external controller 125 implements framing of the data prior to transmission. In some embodiments, the external controller 125 encodes the data prior to transmission in the ultrasound pulse intervals and/or durations, and/or position, etc.

Depending on the nature of the modulation/encoding scheme, responsibility for portions of the encoding process may be shifted out of the transmitter 40 and into the external controller 125. Similarly, responsibility for portions of the decoding process may be shifted out of the receiver 50 and into the internal controller 135.

Any suitable communication protocol may be used. For example, the message, data, or command may be determined by the specific protocol. Optionally, the internal controller 135 may be configured to check all incoming data for integrity using any of a variety of techniques. The protocol may also implement an error detection or error correction logic (e.g. simple parity, checksums, to more complex Hanning code, or other). This can help the receiver side to understand if the message/command/data detected is valid or might be corrupted.

Optionally, a secure communication protocol may be employed by the system e.g., by having the external controller 125 encrypt the data that it sends to the ultrasound transmitter 40 and by having the internal controller 135 decrypt the data that it receives from the ultrasound receiver 50. A wide variety of approaches for implementing this encryption/decryption or another security protocol can be used, the details of which will be apparent to persons skilled in the relevant arts.

To improve coupling between the external unit 120 and the implantable apparatus 100, an ultrasound gel may be interposed between the external unit 120 and the surface of the object (e.g. surface of the subject skin). In addition, the external unit 120 may be positioned so that the ultrasound transducer 42 touches the surface of the object at a location that is close to the location of the implantable apparatus 100. When the implantable apparatus 100 is implanted within a subject's body), the ultrasound transducer 52 is preferably positioned to make contact with tissue within the subject's body.

Notably, whenever the auxiliary apparatus 120 is not touching the surface of the object (e.g. the surface of the skin of a human body) and is not in acoustic contact with the surface of the object, the auxiliary apparatus 120 will not be able to send its commands into the object via ultrasound. This renders the implanted device 150 immune from external control.

One potential drawback of the FIG. 1 embodiment is that, due to the one-way data path, the external controller 125 has no way of verifying if a command that it issued has actually arrived at the internal controller 135. One way to minimize this potential drawback is to have software in the internal controller 135 take into account a possible mistake in the sending of information from the external unit 120 to the implanted device 150.

Figure 2:
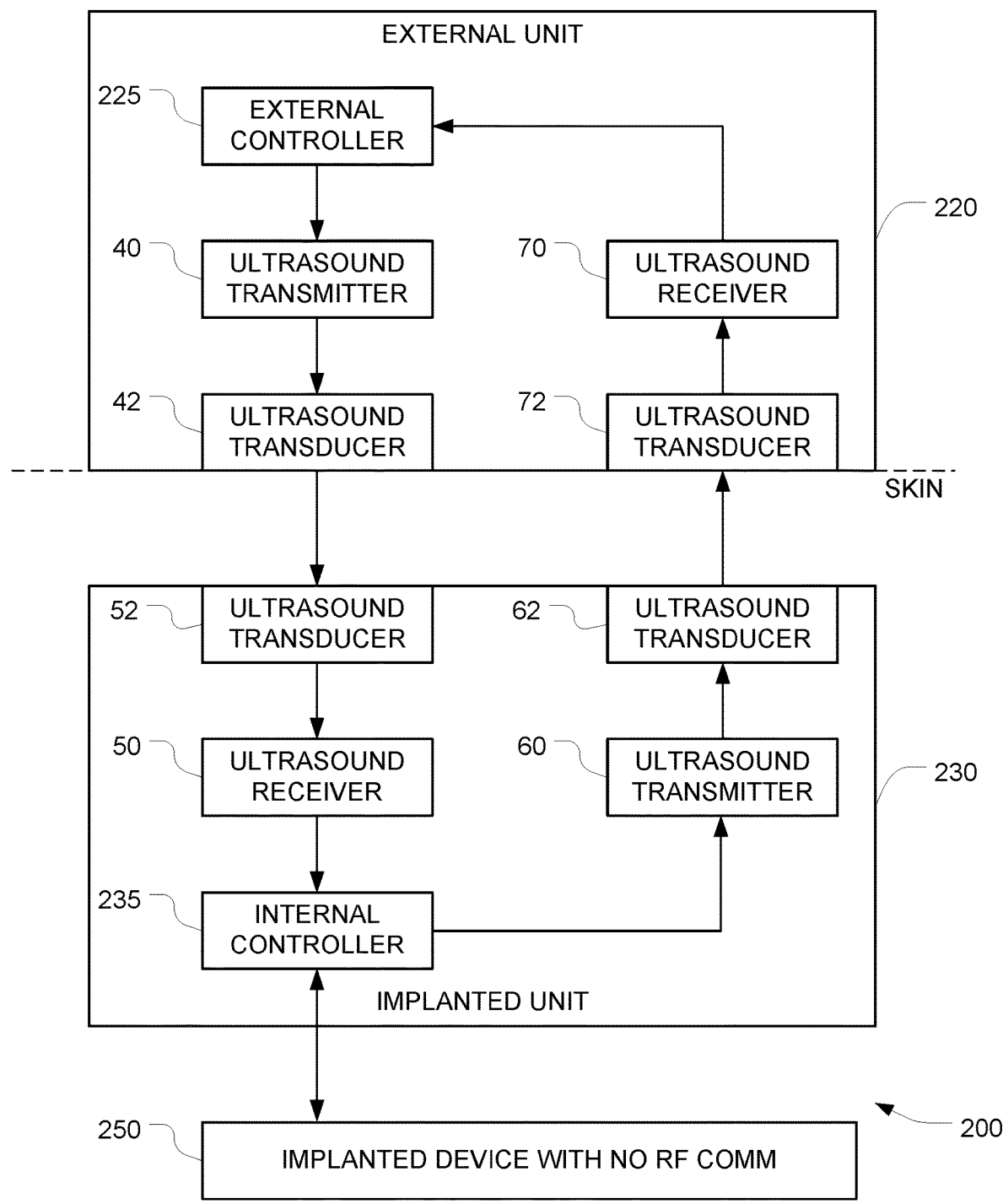
FIG. 2 depicts an example of a system for implementing secure ultrasound communication with an implanted device with an additional ultrasound data path in the opposite direction.

FIG. 2 depicts a way to overcome this potential drawback entirely by adding additional components to the FIG. 1 embodiment. In FIG. 2, the data path from the external controller 225 to the internal controller 235 and into the implanted device 250 is similar to the data path from the external controller 125 to the internal controller 135 and the implanted device 150, as described above in connection with FIG. 1. And the implanted device 250 is similar to the implanted device 150 in the FIG. 1 embodiment. But in the FIG. 2 embodiment, an additional data path in the opposite direction (i.e. from the internal controller 235 to the external controller 225) is provided. This additional data path can be used to verify receipt of commands and to report status of the implanted device 250.

The operation of the internal controller 235 is similar to the operation of the internal controller 135 in the FIG. 1 embodiment, except that the internal controller 235 is configured to also send data in the reverse direction (i.e. towards the external controller 225) and that the external controller 225 is configured to receive that data. This may be accomplished by configuring the internal controller 235 to generate second data that is indicative of receipt of the first data.

In some of these embodiments, the logical loop of communication is "terminated" by one or more communication channels that enable the implanted device 250 to echo back to the external unit 220 information about the received data (i.e., the data that arrived at the internal controller 235). The external controller 225 can then check the echoed data and confirm (e.g., using one or more special commands) that indeed the received command was the right one, and the implanted device 250 can continue and use this command/data/message.

The implantable apparatus 200 in this embodiment has a second ultrasound frequency transmitter 60 that encodes the second data onto a second driving signal, and a third ultrasound transducer 62 that generates a third ultrasound output signal in response to the second driving signal. The third ultrasound output signal has frequency and amplitude characteristics that permit the third ultrasound output signal to reach an external surface of the object (e.g., the subject's skin). Note that while FIG. 2 depicts the first ultrasound transducer 52 and the third ultrasound transducer 62 as separate blocks, a single physical ultrasound transducer may serve as both the first ultrasound transducer 52 and the third ultrasound transducer 62.

The auxiliary apparatus 220 has a fourth ultrasound transducer 72 arranged to detect the third ultrasound output signal when the fourth ultrasound transducer 72 is placed in acoustic contact with a surface of the object, and to generate a fourth electrical output signal that corresponds to the third ultrasound output signal. Note that while FIG. 2 depicts the second ultrasound transducer 42 and the fourth ultrasound transducer 72 as separate blocks, a single physical ultrasound transducer may serve as both the second ultrasound transducer 42 and the fourth ultrasound transducer 72.

The auxiliary apparatus 220 also includes a second ultrasound frequency receiver 70 that generates, based on the fourth electrical output signal, fourth data. This fourth data is provided to the second controller, and the fourth data has some correspondence to the second data so that when the external controller 225 receives the fourth data, the external controller 225 will know that the internal controller 235 has received the first data.

Figure 3:
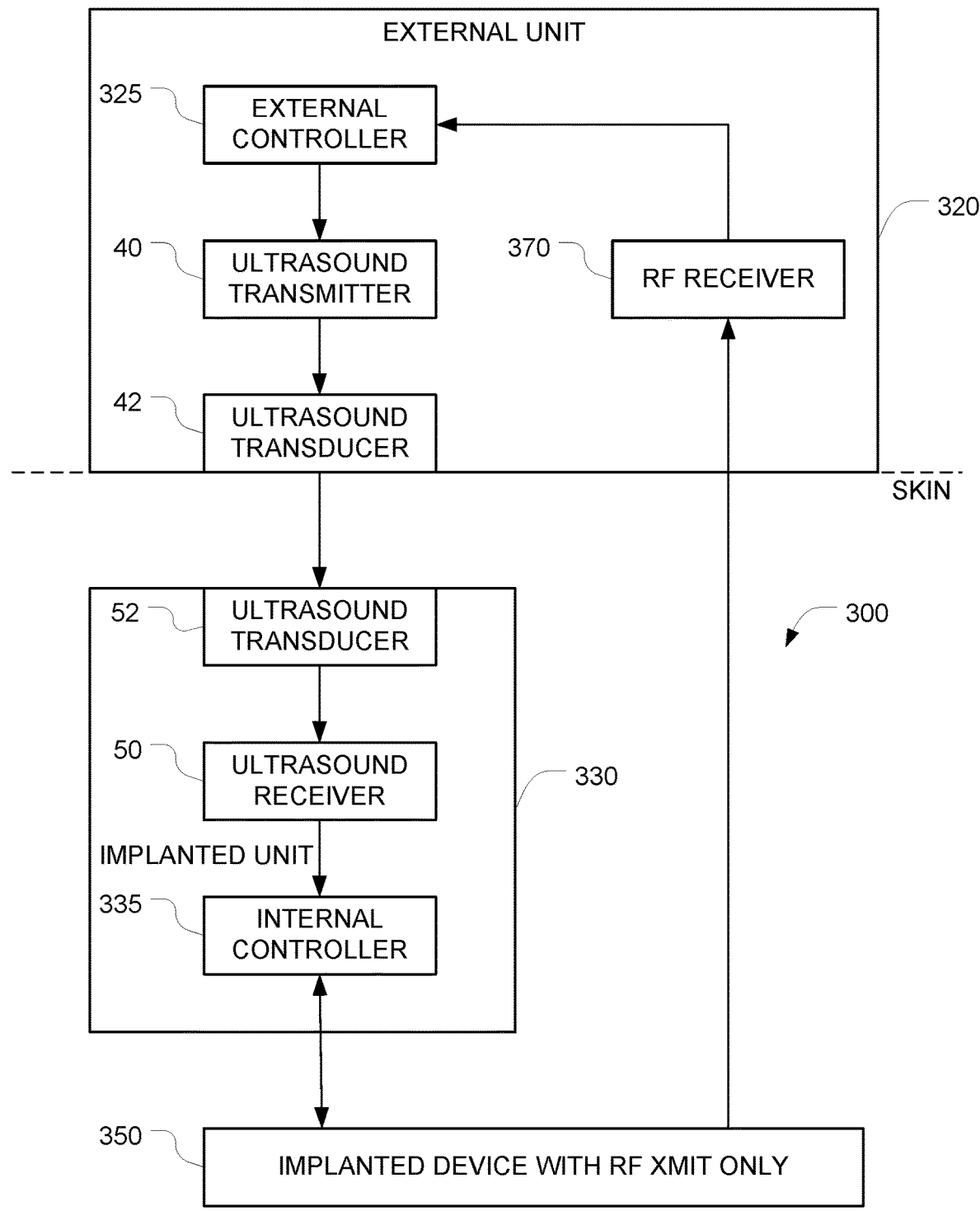
FIG. 3 depicts an example of a system for implementing secure ultrasound communication with an implanted device with an additional RF data path in the opposite direction.

FIG. 3 depicts another embodiment that adds additional components to the FIG. 1 embodiment to overcome the potential drawback noted above. In the FIG. 3 embodiment, the auxiliary apparatus 320 further includes an RF receiver 370, and the implantable apparatus 350 includes an RF transmitter capable of communicating with the RF receiver 370.

In FIG. 3, the data path from the external controller 325 to the internal controller 335 and into the implanted device 350 is similar to the data path from the external controller 125 to the internal controller 135 and the implanted device 150, as described above in connection with FIG. 1. And the implanted device 350 is similar to the implanted device 150 in the FIG. 1 embodiment. But in the FIG. 3 embodiment, an additional data path in the opposite direction (i.e. from the implanted device 350 to the external controller 225) is also provided. This additional data path can be used to verify receipt of commands and to report status of the implanted device 350.

The operation of the internal controller 335 is similar to the operation of the internal controller 135 in the FIG. 1 embodiment. Here, the implanted device 350 has an RF transmitter, and that RF transmitter is configured to send data in the reverse direction (i.e. towards the external controller 325) and that the external controller 325 is configured to receive that data. This may be accomplished by configuring the implanted device 350 to generate return data that is indicative of receipt of the first data. Notably, the implanted device 350 does not have the ability to receive data via RF (e.g., because it has no corresponding hardware to perform that function or because the relevant hardware is disabled). As a result, it will be impossible to control the implanted device 350 by beaming commands into the implanted device 350 via RF.

One example of signal flow for using the FIG. 3 embodiment is as follows. In this discussion, we assume that a user (e.g., a doctor or family member or the person with the implant—someone close and authorized by definition) is using the external unit 320. When the external unit 320 is close (e.g., within RF range) to the implant, the external unit 320 can receive RF communication from the implanted device 350—as it is done in conventional RF communication implants like pacemakers. The user can configure and control the external unit 320 via a keyboard or touch screen or buttons embedded the external unit 320. The external unit 320 software (which runs on the external controller 325) can process authentication of the user—as any normal authentication that any computer software can implement. The user can direct the external unit 320 to present data received from the implant via RF communication. The user can direct the external unit 320 to configure/program/send data to the implant by using the external unit 320 user interface.

The external unit 320 can send data to the implanted device 350 via the ultrasound data link only if the external unit 320 is touching the human body (with no air gap between the external unit 320 and the human body). If an air gap exists between the external unit 320 and the human body, the information from the external unit 320 will not be able to get to its destination (i.e., the implant), due to the absence of a communication link.

In some embodiments, the external controller 325 and the implanted device 350 are programmed to authenticate the message sent to the implanted device 350 and feedback the received command or data received via the ultrasound data channel back to the external controller 325 (via the RF channel), and request the user to approve (double check) the command that was sent to the implanted device 350. In some embodiments, the internal controller 335 may be programmed to accept the configuration data (as was sent before) only after it receives a second confirmation command from the user (i.e., the confirmation command, which is also sent via the ultrasound data path).

Any data from the external unit 320 can be sent to the unsecure internet by communication over a suitably programmed secure one-way-only communication link. It is true that the direct RF communication from the implant can be received by any RF receiver device positioned near the human/implant. However, this is not considered a security concern, because in the FIG. 3 embodiment, it is read only information. More specifically, in the FIG. 3 embodiment, it will not be possible to write to the implanted device 350 via RF communication as the implanted device 350 does not have a RF receiver. In these embodiments, the RF hardware is configured so that the external unit 320 has only a RF receiver 370 and the implanted device 350 has only a RF transmitter (this configuration makes transmission from the outside world into the implant impossible). In these embodiments, it will not be possible to write to the external unit 320 from the network, as all communication from the external unit 320 to the unsecured internet will be done via the secure one-way-only device.

Figure 4:
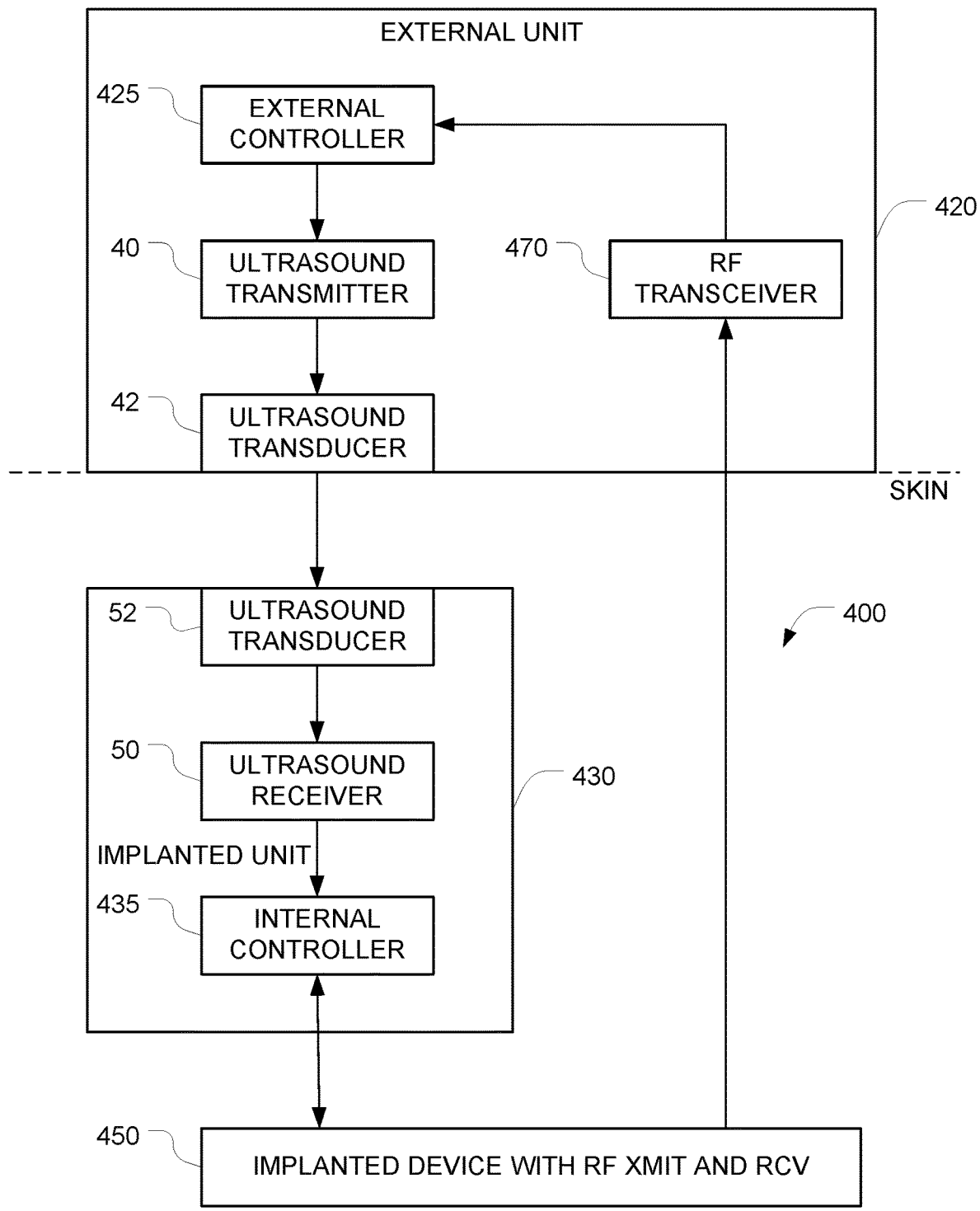
FIG. 4 depicts an example of a system for implementing secure communication with an implanted device using signals that arrive via RF, but only after communications have been enabled using an ultrasound signal.

FIG. 4 depicts an example of a system for implementing secure communication with an implanted device 450 that has been implanted into an object (e.g., a human body). In this embodiment, it is possible to control the implanted device using signals that arrive via RF, but only under certain circumstances. More specifically, in its default state, the implanted system is programmed to ignore all commands that arrive via RF. But the ability to accept commands that arrive via RF can be turned on by sending an appropriate command to the implanted unit via an ultrasound data path. Once RF communication is turned on, communication with the implanted device can proceed in a conventional manner.

After a single communication session has ended (e.g. after a predetermined time has elapsed or after an "end session" command is received), the implanted system reverts to its default state in which it will no longer accept commands via RF.

The system includes an implantable apparatus 400 and an external unit 420 (also referred to herein as an auxiliary apparatus). The implantable apparatus 400 includes the implantable device 450 and additional implanted components 430, both of which are configured for implantation into an object (e.g., a human body). Examples of devices that can be implanted are similar to those described above in connection with FIG. 1. The implantable device 450 has at least one control input, and the implantable device is controllable by applying at least one electrical control signal to the at least one control input. The implantable apparatus 400 is configured so that in its default state, it ignores all attempts to control the implantable device 450 via RF signals. This may be accomplished, for example, by starting with a conventional implanted device (e.g., a pacemaker) that is controllable via RF signals, and disabling the RF section of the device under software control.

The implantable device 450 has an RF transceiver and at least one hardwired control input, and the implantable device is controllable by applying at least one electrical control signal to the at least one hardwired control input. And it is this at least one hardwired control input that is used to switch the implantable device 450 from its default state (in which it ignores RF commands) to an "RF communication enabled" state. Note that the software and or hardware of the implantable device 450 must be configured to respond to commands that are received via this at least one hardwired control input.

In the FIG. 4 embodiment, the signal path that is used to control the state of the implanted device 450 comprises the additional implanted components 430. In the illustrated example, these additional implanted components 430 comprise a first ultrasound transducer 52, a first ultrasound frequency receiver 50, and a first controller 435 (also referred to herein as an internal controller). These additional implanted components 430 may be housed in a housing that is separate from the housing of the implanted device 450. In alternative embodiments, the implanted device 450 and the additional implanted components 430 may be housed together in a single housing.

Operation of the first ultrasound transducer 52 and the first ultrasound frequency receiver 50 is similar to the operation of the corresponding elements in FIG. 1, as described above. The ultrasound receiver 50 outputs first data corresponding to commands that have been encoded onto the first incoming ultrasound signal. This first data is provided to the first controller 435. The first controller 435 is configured to (a) generate, based on the first data, the at least one electrical control signal, and (b) to apply the generated at least one electrical control signal to the at least one control input of the implantable device 450. The implantable device 450 is configured to keep its RF transceiver disabled until the at least one electrical control signal generated by the first controller 435 includes an enable command, and to temporarily enable its RF transceiver after the at least one electrical control signal generated by the first controller 435 includes an enable command.

Based on the description of the implantable apparatus 400 above, it will be apparent that in order to control the implantable apparatus 400, a pathway must be provided for delivering ultrasound signals to the ultrasound transducer 52 in the implantable apparatus 400. In the FIG. 4 embodiment, this is accomplished by the auxiliary apparatus 420, which remains outside of the object (e.g. outside of the human body).

The operation of the auxiliary apparatus 420 is similar to the operation of the auxiliary apparatus 120 described above in connection with FIG. 1, except that instead of using the external controller to directly control the operation of the implanted device 450, the external controller sends an enable command to the implanted device 450 via a data path that is similar to the data path described above in connection with FIG. 1. Once this enable command is received by the implanted device 450, the implanted device 450 will switch from its default state (in which it ignores commands that arrive via RF) to its "RF communication enabled" state.

The signal path from the external controller 425 to the internal controller 435 is similar to the path between the external controller 125 and the internal controller 135 described above in connection with FIG. 1. And as in FIG. 1, whenever the auxiliary apparatus 420 is not touching the surface of the object (e.g., the surface of the skin of a human body) and is not in acoustic contact with the surface of the object, the auxiliary apparatus 420 will not be able to send its commands into the object via ultrasound. This renders the implanted device 450 immune from external control.

In this FIG. 4 embodiment, once communication is set up between the external unit 420 and the implanted device 450, subsequent communications between the RF transmitter and the RF receiver may be enabled for a preset duration of time. This alternative may be advantageous because RF communications can be implemented using conventional hardware, and can achieve higher data rates than ultrasound communications. In alternative embodiments for implementing two-way communication, the RF transceiver 470 may be replaced with a RF transmitter and a separate RF receiver.

In any of the embodiments described herein, the implanted device may include one or more implanted devices designed to measure or monitor physiological, chemical, or physical parameters, etc. or to affect some physiological activity such as heart rate, neural activity, etc. The embodiments described herein provide a safe way to control from the outside or from another implanted device, the activity of the implanted devices, for example to alter the heart rate, cardiac stimulation timing, timing of sensor (pressure, etc.), reporting etc. from the outside. Specifically, the system does not allow any interference with the implant function by an unauthorized agent.

In any of the embodiments described herein, the frequency of the ultrasound used for communication is preferably between 0.5-20 MHz, and more preferably between 1-5 MHz or between 1-3 MHz. In some preferred embodiments, ultrasound with a frequency of around 2 MHz is used. These frequency ranges are preferred because low frequency ultrasound (e.g. 20-100 kHz) can cross the air/body interface with relatively low losses, and therefore may not provide the desired level of security. In contrast, the corresponding losses for higher frequency ultrasound (e.g. on the order of 1-5 MHz) are large enough to provide the desired level of security. As for the upper limit, the frequency of the ultrasound is preferably below 10 MHz, because higher frequencies will undergo significant attenuation as they pass through tissue in the body, to the point where the signal may not be able to reach the implant.

The ultrasound power is preferably within the allowed range, preferably less than one tenth the maximal allowed power. The depth of penetration of 2 MHz signals is sufficient for any intra-body location. The ultrasound beam generated should preferably be relatively wide such that there is no need to point the beam axis exactly at the implant. Examples of suitable transducers include single element, small diameter (2-10 mm) Piezo electric elements. The transducer's contact with the subject's skin is preferably mediated by conventional ultrasound gel. The transducer can be hand held or can have a patch like structure and be attached to the skin by an adhesive like an ECG electrode.

In some situations, two or more implantable devices may be implanted into a single object (e.g., into a single human body). In these situations, it may be desirable to communicate with only a desired one of the implants. One way to achieve this is to separate the implants in space, and rely on directionality of the ultrasound beam to direct the communication to the desired destination. In case of a body containing a few implants, one can wake-up the desired implant alone by using a second transducer that outputs an ultrasound beam, for example one having a beam with a diameter of a few mm, beaming or aiming the ultrasound energy to the specific area where the selected first transducer is located. In these embodiments, the distance between the implants should be such that the distance between them will enable safe operation without crosstalk.

Another way to accomplish this is to assign a unique passive address to each implanted device. This may be accomplished, for example, by adding a Piezo electric element to each of the implanted devices, wherein each Piezo electric element has a different operational frequency. For example, one Piezo electric element can operate at f1=1.2 MHz and the other Piezo electric element can operate at f2=1.8 MHz). In these embodiments, each implant will have a different operational (peak or resonance) frequency.

Although more than one implanted device within "listening" range may receive the signals, due to differences in the resonant frequencies and differences in timing of the applied sequence, non-target implants will not be activated. Thus, by using two or more frequencies and dedicated durations for the sequence, one can build a specific implant passive address. In these embodiments, the external unit can be designed to activate the desired implant by outputting the predetermined sequence at the relevant frequencies. For example, in these embodiments, the external unit can generate a wake up signal by transmitting a few activations of the desired frequency (i.e., either a few activations of f1 or f2) for specific durations.

Figure 5:
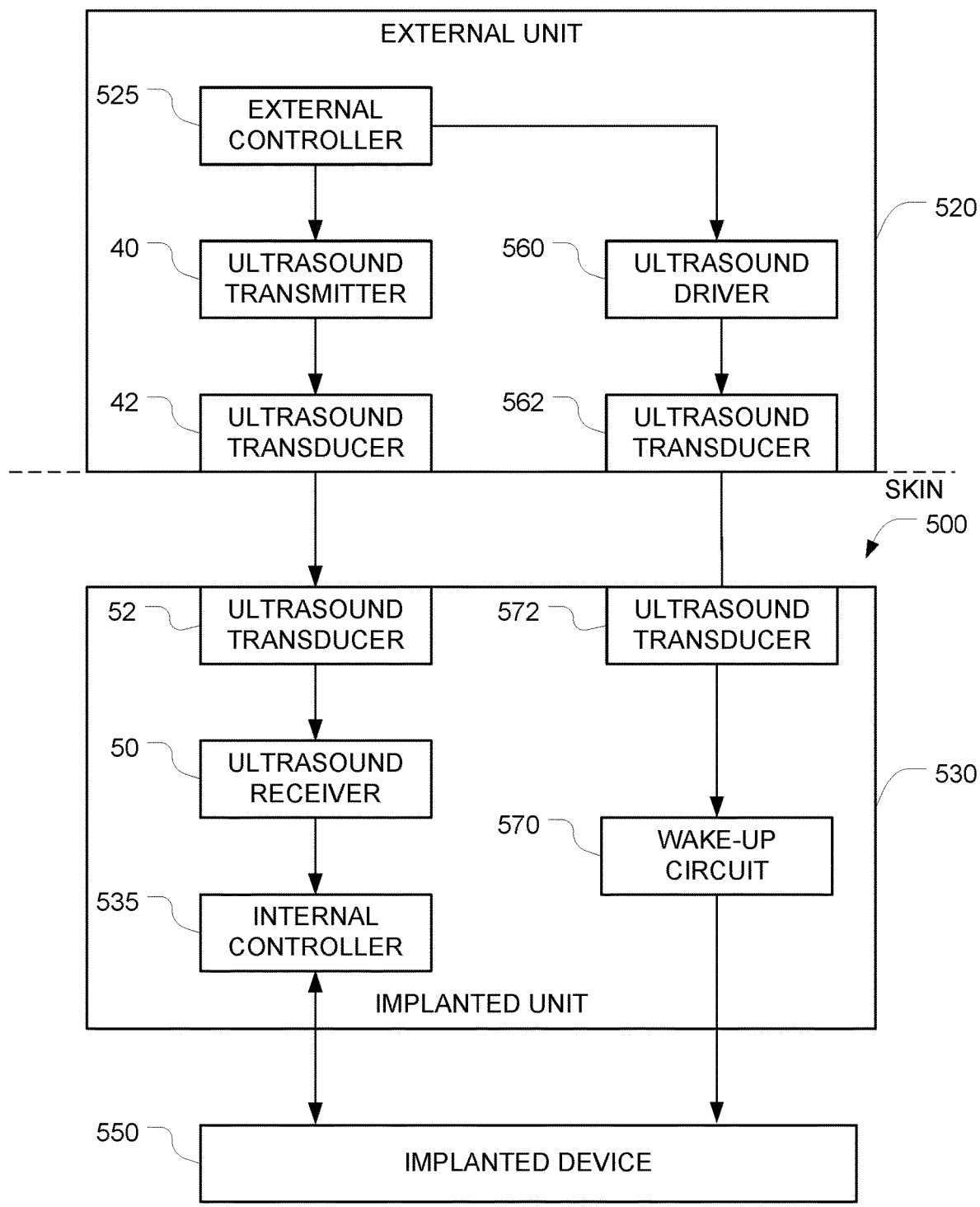
FIG. 5 is a block diagram that shows how wake-up circuitry can be incorporated into any of the above embodiments.

FIG. 5 is a block diagram that shows how this type of wake-up circuitry can be incorporated into the external unit and the implanted unit. In this embodiment, the components 40-50 will operate in the same way as described above in connection with FIG. 1; and the internal controller 535 and implanted device 550 operate in the same way as the corresponding controller 135 and implanted device 150 in the FIG. 1 embodiment. The operation of the external controller 525 is also similar to the external controller 125 in the FIG. 1 embodiment. However, external controller 525 in this FIG. 5 embodiment adds additional functionality to control the wake-up circuitry. More specifically, the external controller 525 can selectively issue a command to activate the ultrasound driver 560. The ultrasound driver 560 generates an ultrasound frequency signal that is applied to the ultrasound transducer 562. In response, the ultrasound transducer 562 generates ultrasound waves (i.e., a third ultrasound output signal). The external unit 520 is positioned in contact with the surface of the object (e.g., with the service of a human's skin) so that the ultrasound waves can enter the object.

The ultrasound waves travel through the object until they reach the fourth ultrasound transducer 572 within the implanted unit 530. The fourth ultrasound transducer 572 converts the incoming ultrasound waves to an electrical signal, and this electrical signal is applied to the wake-up circuit 570. The wake-up circuit 570 harvests ultrasound energy arriving at the fourth ultrasound transducer 572 and generates a wake-up signal for the implanted device 550 from the harvested ultrasound energy. In alternative embodiments (not shown), various components within the implanted unit 530 (e.g. the internal controller 535) may remain in a sleep mode (in addition to or in place of the implanted device 550) until they are activated by the wake-up circuit 570.

Note that while FIG. 5 depicts the first ultrasound transducer 52 and the fourth ultrasound transducer 572 as separate blocks, a single physical ultrasound transducer may serve as both the first ultrasound transducer 52 and the fourth ultrasound transducer 572. Similarly, while FIG. 5 depicts the second ultrasound transducer 42 and the third ultrasound transducer 562 as separate blocks, a single physical ultrasound transducer may serve as both the second ultrasound transducer 42 and the third ultrasound transducer 562.

Figure 6:
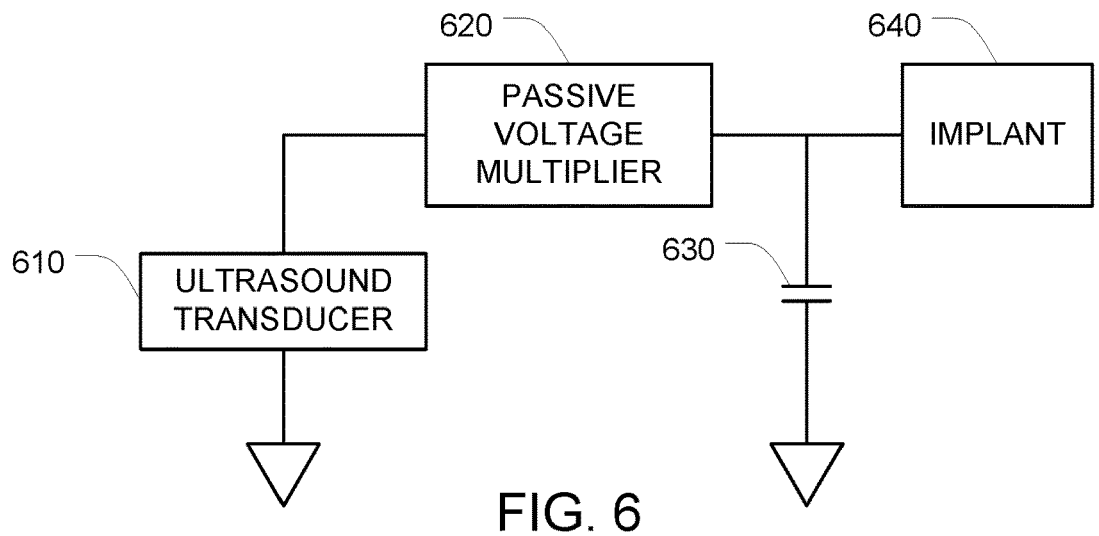
FIG. 6 is a schematic diagram of a suitable wake-up circuit that may be used in connection with FIG. 5.

FIG. 6 is a schematic diagram of a wake-up circuit that may be used in these embodiments. The depicted wake-up circuit relies on a passive voltage multiplier 620 to process the electrical signal that is output from transducer 610. The passive voltage multiplier circuit is configured so that the output voltage will only rise above a predetermined threshold if the correct sequence arrives from the external unit.

In these embodiments, the implanted ultrasound transducer 610 is activated by ultrasound waves that arrive from another ultrasound transducer (not shown) positioned externally, but in contact with the body surface. The external transducer is operated in pulse mode at clinically used intensities and frequencies, preferably at 1-5 MHz. The sound waves generated by the second transducer can be expected to generate in the first passive transducer AC pulses in the range of mV to 1 V.

Assume that we start with a value of 0.1 V. Connecting this transducer to a passive voltage multiplier having a cascade of 5-10 capacitor-rectifier pairs will produce about a 1V output pulse in response to a corresponding AC pulse (for example a 1 MHz signal, in the range of 10-50 μS).

When the output of the passive voltage multiplier 620 causes the voltage on the capacitor 630 to exceed a threshold, voltage on that capacitor 630 will rise to a sufficient level to activate the implant 640. This voltage level will be sufficient to turn on a device that is in the off state. Once turned on the device/implant will accept control signals (For example RF, ultrasound, optic, etc.) that control it. The device (implant) can stay on for a preset period of time or remain on till turned off by an RF or other signal.

Suitable wake-up systems may also be implemented by harvesting ultrasound energy. When a piezo electric element (PZT) is exposed to ultrasound energy it generates electricity. As long at the ultrasound energy continues to arrive, the electrical energy/voltage derived from the PZT continues. If a capacitor is connected to the output of the PZT, the output of the PZT can be collected in the capacitor, and when the level of the voltage accumulated in the capacitor reaches a specific threshold, this event can be used to trigger the operation of an electrical circuit that resides in the implant.

In other embodiments, a unique semi-active identity is assigned to each implant. The logic flow in these embodiments is to have the communication part (and/or any other part that is in sleep mode and can get a wakeup signal from the external unit) of the implants wait passively for an ultrasound wake up analog signal. All implants will respond to the same analog wakeup signal and switch into a partial wakeup state. The purpose of this partial wakeup state is to determine the destination of the communications that are currently arriving. The partial wakeup will activate an initial and low power receiver, by using power from the implant battery. The external unit will send a follow-up code (i.e., subsequent to the initial analog wakeup signal). A unique code is assigned to each implant. All implants will receive the code; but only one will recognize it as a matching code and will activate its own communication part in response (until it eventually reverts to the sleep mode). All other destinations will fail to recognize the code and will return to sleep mode.

Figure 7:
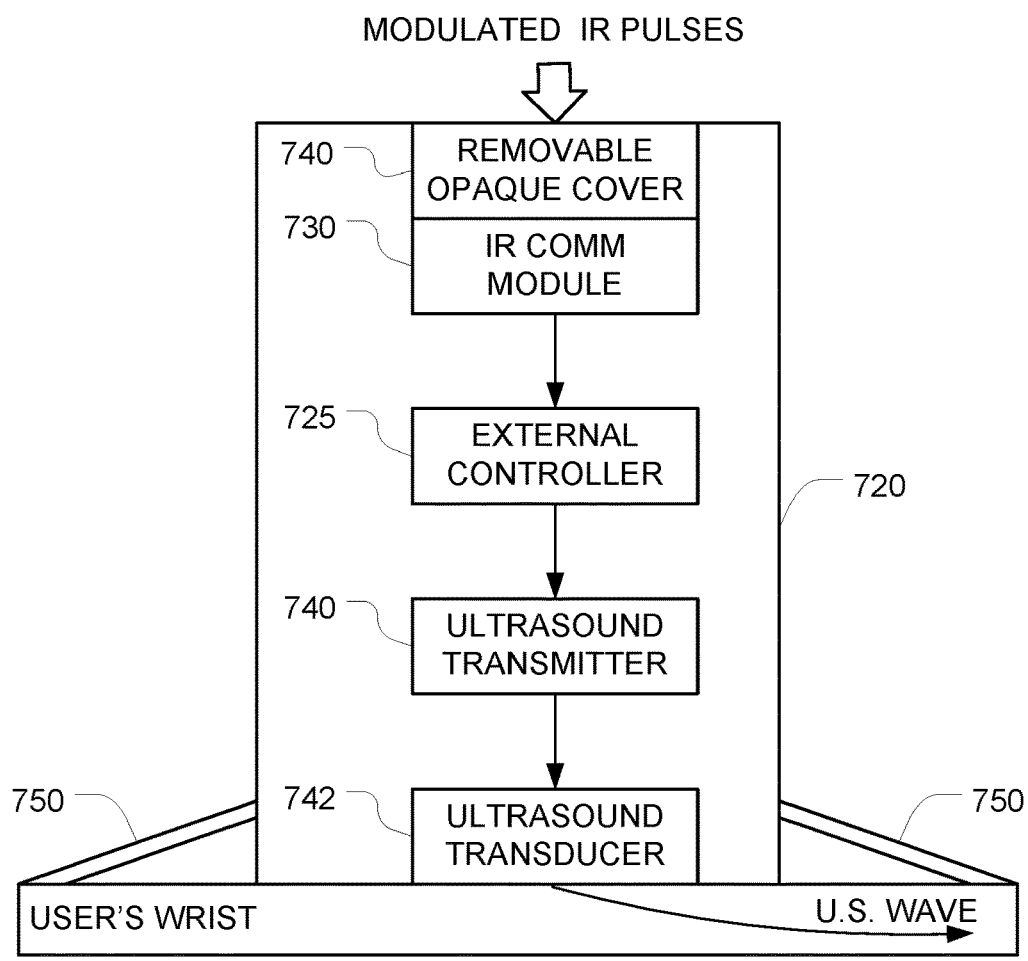
FIG. 7 depicts an auxiliary interface apparatus that facilitates communication with ultrasound-controlled implants using an optical-to-ultrasound intermediary.

FIG. 7 depicts an auxiliary interface apparatus that facilitates communication with ultrasound-controlled implants using an optical-to-ultrasound intermediary. This embodiment provides the ability to communicate with the implant without the need to bring a new ultrasound transducer into contact with the patient's body. Instead, this embodiment relies on an ultrasound transducer 742 that is constantly kept in contact with the user's body. The implant is controlled via ultrasound as described above in connection with FIGS. 1-5.

In this embodiment, a Wearable Device (WD) 720 is used to generate the ultrasound based instruction waves. Conventional devices such as smart watches are ordinarily worn in intimate contact with the subject/patient's body, for example on the wrist or forearm. This embodiment takes advantage of this situation and adds an ultrasound transducer 742 and supporting hardware to a smart watch so that the ultrasound transducer 742 makes contact with the surface of the person's skin. When this ultrasound transducer 742 is used to generate ultrasound waves, those ultrasound waves will enter the person's body at the wrist, and easily travel within the body tissues to reach an implant that is located a significant distance away from the WD 720. Optionally, the contact between the WD 720 and body can be improved by applying appropriate ultrasound gel to the contact area.

In alternative embodiments, instead of providing communication between a single WD 720 and an implant, similar hardware may also be used to communicate between two or more WD devices that are affixed to two different portions of a person's body (or two different portions of a different object).

Operation of the WD 720 is similar to the operation of the external unit 120 described above in connection with FIG. 1; and the operation of the external controller 725, the ultrasound transmitter 740, and the ultrasound transducer 742 is similar to the operation of the corresponding components 125, 40, and 42 in the FIG. 1 embodiment. However, in the FIG. 7 embodiment, control of the WD 720 is initiated using an optical communication module such as the infrared communication module 730.

The WD is activated via a set of instructions that are encoded into incoming light (e.g., visible or IR). The instructions can be in the form of light modulation or light pulses in which the instructions are encrypted. The advantage of such control using light is that it can be used without contact but cannot be used from a distance if the subject is located in a room or the like. Furthermore, a simple opaque cover 740 positioned on the WD will block any unauthorized control. The WD is preferably equipped, beneath its exposed surface, with an optical communication module 730 that translates the incoming optical signals into electric signals. The communication between the outside world and the optical communication module 730 may be implemented using any conventional optical communication protocol (e.g., IrDA).

The output of the optical communication module 730 is fed to the external controller 725 over any appropriate data link (e.g., USB). The external controller 725 then converts these signals into data that is fed into the ultrasound transmitter 740, as described above in connection with FIG. 1. The output of the ultrasound transmitter 740 is used to drive the ultrasound transducer 742, also as described above in connection with FIG. 1. The ultrasound transducer 742 can then transmit a corresponding ultrasound wave into the user's body. Optionally, the WD 720 may be affixed to the user's body using one or more straps 750.

In alternative embodiments, instead of using modulated light pulses to provide access to the external controller 725, an alternative communication approach (e.g., sound waves, mechanical vibration) or an alternative user interface (e.g. buttons or touch screen) may be used to provide access to the external controller 725.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A system for implementing secure communication, the system comprising:
   an implantable apparatus including
      an implantable device configured for implantation into a body, the implantable device having at least one control input, wherein the implantable device is controllable by applying at least one electrical control signal to the at least one control input,
      a first ultrasound transducer that generates a first electrical output signal in response to a first incoming ultrasound signal,
      a first ultrasound frequency receiver that generates, based on the first electrical output signal, first data corresponding to commands that have been encoded onto the first incoming ultrasound signal, and
      a first controller configured to (a) generate, based on the first data, the at least one electrical control signal, and (b) to apply the generated at least one electrical control signal to the at least one control input of the implantable device,
   wherein the implantable apparatus is configured to ignore all attempts to control the implantable device via RF signals; and
   an auxiliary apparatus including
      a second controller configured to generate commands for controlling the implantable device,
      a first ultrasound frequency transmitter that encodes the commands generated by the second controller onto a first driving signal, and
      a second ultrasound transducer that generates a second ultrasound output signal in response to the first driving signal.

2. The system of claim 1, wherein the implantable device lacks hardware that is capable of receiving control instructions via RF signals.

3. The system of claim 1, wherein the implantable device includes an RF receiver that has been disabled.

4. The system of claim 1,
wherein the first controller is further configured to generate second data that is indicative of receipt of the first data,
wherein the implantable apparatus further comprises (a) a second ultrasound frequency transmitter that encodes the second data onto a second driving signal, and (b) a third ultrasound transducer that generates a third ultrasound output signal in response to the second driving signal, and
wherein the third ultrasound output signal has frequency and amplitude characteristics that permit the third ultrasound output signal to reach an external surface of the body.

5. The system of claim 4,
wherein the auxiliary apparatus further includes a fourth ultrasound transducer arranged to detect the third ultrasound output signal when the fourth ultrasound transducer is placed in acoustic contact with a surface of the body, and to generate a fourth electrical output signal that corresponds to the third ultrasound output signal,
wherein the auxiliary apparatus further includes a second ultrasound frequency receiver that generates, based on the fourth electrical output signal, fourth data,
wherein the fourth data is provided to the second controller, and
wherein the fourth data corresponds to the second data.

6. The system of claim 1, wherein the auxiliary apparatus further includes an RF receiver, and wherein the implantable apparatus further includes an RF transmitter capable of communicating with the RF receiver.

7. The system of claim 1,
wherein the auxiliary apparatus further includes (a) a driver that generates an ultrasound frequency output and (b) a third ultrasound transducer that generates a third ultrasound output signal in response to the ultrasound frequency output generated by the driver, and wherein the second controller is configured to selectively activate the driver, and
wherein the implantable apparatus further comprises a fourth ultrasound transducer operatively connected to a wake-up circuit, wherein the wake-up circuit is configured to (i) harvest ultrasound energy arriving at the fourth ultrasound transducer and (ii) generate a wake-up signal for the implanted device from the harvested ultrasound energy.

8. The system of claim 1, wherein the body is a human body.

9. The system of claim 1, wherein the first ultrasound frequency transmitter has an operating frequency between 1-5 MHz.

10. An apparatus comprising:
an implantable device configured for implantation into a body, the implantable device having at least one control input, wherein the implantable device is controllable by applying at least one electrical control signal to the at least one control input;
an ultrasound transducer that generates an electrical output signal in response to an incoming ultrasound signal;
an ultrasound frequency receiver that generates, based on the electrical output signal, first data corresponding to commands that have been encoded onto the incoming ultrasound signal; and
a controller configured to (a) generate, based on the first data, the at least one electrical control signal, and (b) to apply the generated at least one electrical control signal to the at least one control input of the implantable device,
wherein the implantable apparatus is configured to ignore all attempts to control the implantable device via RF signals.

11. The implantable apparatus of claim 10, wherein the implantable device lacks hardware that is capable of receiving control instructions via RF signals.

12. The implantable apparatus of claim 10, wherein the implantable device includes an RF receiver that has been disabled.

13. The implantable apparatus of claim 12, wherein the RF receiver is disabled by shielding that prevents RF signals from arriving at the RF receiver.

14. The implantable apparatus of claim 10, wherein the implantable device comprises a pacemaker.

15. The implantable apparatus of claim 10, wherein at least one of the ultrasound frequency receiver and the controller is configured to implement a secure communication protocol.

16. The implantable apparatus of claim 10,
wherein the controller is further configured to generate second data that is indicative of receipt of the first data,
wherein the implantable apparatus further comprises (a) an ultrasound frequency transmitter that encodes the second data onto a driving signal, and (b) an ultrasound transducer that generates an ultrasound output signal in response to the driving signal, and
wherein the ultrasound output signal has frequency and amplitude characteristics that permit the ultrasound output signal to reach an external surface of the body.

17. The implantable apparatus of claim 10, wherein the implantable device includes an RF transmitter capable of communicating with an RF receiver that is positioned outside the body.

18. The implantable apparatus of claim 10, wherein the body is a human body.

19. A system for implementing secure communication, the system comprising:
an implantable apparatus including
an implantable device configured for implantation into a body, the implantable device having an RF transceiver and at least one control input, wherein the implantable device is controllable by applying at least one electrical control signal to the at least one control input,
a first ultrasound transducer that generates a first electrical output signal in response to a first incoming ultrasound signal,
a first ultrasound frequency receiver that generates, based on the first electrical output signal, first data corresponding to commands that have been encoded onto the first incoming ultrasound signal, and
a first controller configured to (a) generate, based on the first data, the at least one electrical control signal, and (b) to apply the generated at least one electrical control signal to the at least one control input of the implantable device,
wherein the implantable device is configured to keep the RF transceiver disabled until the at least one electrical control signal generated by the first controller includes an enable command, and to temporarily enable the RF transceiver after the at least one electrical control signal generated by the first controller includes an enable command; and an auxiliary apparatus including
- a second controller configured to generate commands for controlling the implantable device,
- a first ultrasound frequency transmitter that encodes the commands generated by the second controller onto a first driving signal, and
- a second ultrasound transducer that generates a second ultrasound output signal in response to the first driving signal.

20. The system of claim 19, wherein the auxiliary apparatus further includes an RF transceiver.

21. The system of claim 19, wherein the body is a human body.

22. The system of claim 19, wherein at least one of the first ultrasound frequency receiver and the first controller is configured to implement a secure communication protocol.

23. The system of claim 19, wherein the first ultrasound frequency transmitter has an operating frequency between 1-5 MHz.

* * * * *